(12) United States Patent
Matthiessen

(10) Patent No.: US 6,650,417 B2
(45) Date of Patent: Nov. 18, 2003

(54) OPTICAL ABSORPTION MEASURING INSTRUMENT

(75) Inventor: Hans Matthiessen, Bad Schwartau (DE)

(73) Assignee: Dräger Safety AG & Co. KGaAM, Lübeck (DE)

(*) Notice: Subject to any disclaimer, the term of this patent is extended or adjusted under 35 U.S.C. 154(b) by 61 days.

(21) Appl. No.: 10/105,766

(22) Filed: Mar. 25, 2002

(65) Prior Publication Data
US 2003/0002044 A1 Jan. 2, 2003

(30) Foreign Application Priority Data
Jun. 29, 2001 (DE) .......................... 101 31 724

(51) Int. Cl.$^7$ .............................................. G01N 21/00
(52) U.S. Cl. ................... 356/436; 356/440; 250/343; 250/339.12
(58) Field of Search ................. 356/432, 433, 356/434, 435, 436, 437, 438, 439, 440, 244, 246; 250/341.4, 343, 344, 373, 339.05, 339.72

(56) References Cited

U.S. PATENT DOCUMENTS 3,515,489 A * 6/1970 Chisholm .................. 356/432
3,586,441 A * 6/1971 Smith et al. ............... 356/320
3,756,726 A * 9/1973 Astheimer .................. 356/434
4,175,864 A * 11/1979 Gilby ........................ 356/326
4,730,922 A * 3/1988 Bach et al. .................. 356/73
5,550,375 A * 8/1996 Peters et al. ............... 250/343
5,729,333 A * 3/1998 Osten et al. ................. 356/39
5,777,735 A * 7/1998 Reagen ...................... 356/451

FOREIGN PATENT DOCUMENTS

DE   37 36 673 C2   11/1989

* cited by examiner

Primary Examiner—Hoa Q. Pham
(74) Attorney, Agent, or Firm—McGlew and Tuttle, P.C.

(57) ABSTRACT

An optical absorption measuring instrument for determining the percentage of a component in a fluid shall be improved such that changes in the measuring radiation caused by drift or temperature have only a limited effect on the measuring result. Provisions are made for deflecting the measuring beams (10, 11) from a radiation source (4) to a detector (5) by at least two plane mirrors (71, 72), which are positioned such that the measuring beams (10, 11) emitted by the radiation source (4) are deflected to the detector (5). The surface of each plane mirror (71, 72) is dimensioned to be such that its illuminated surface in the area of the detector (5) is larger than the receiving surface (12) of the detector (5).

20 Claims, 2 Drawing Sheets

OPTICAL ABSORPTION MEASURING INSTRUMENT

FIELD OF THE INVENTION

The present invention pertains to an optical absorption measuring instrument for determining the percentage of a component in a fluid.

BACKGROUND OF THE INVENTION

Optical absorption measuring instruments, e.g., in the form of infrared optical measuring instruments, measure the absorption of infrared beams at a wavelength specific of the component to be detected. The amount of the absorption is an indicator of the percentage of the component in the fluid. There are various designs of such measuring instruments with an infrared radiation source or with a plurality of infrared radiation sources, with the measuring beam passing through an open or closed measuring chamber once or several times. The measuring beam reaches a detector or a plurality of detectors, which are sensitive to the corresponding infrared wavelengths. If a plurality of detectors are used, one of which is a measuring detector and the other a reference detector, the measuring beam is distributed possibly uniformly among the detectors. So-called beam splitters are used to split the measuring beam.

An infrared optical measuring instrument of this type has been known from DE 37 36 673 C2. The measuring beam emitted by an infrared radiation source passes through a measuring chamber, in which the gas component, whose concentration is to be monitored, is located. A ray beam emitted by a radiation source is reflected back by means of two spherical mirrors, which are arranged opposite the radiation source, and is imaged as a focused luminous beam on a detector, which is located at the said limiting surface of the measuring chamber as the radiation source. The individual luminous beams now reach the detector at different reflection angles. The drawback of the prior-art device is that the optical imaging on the receiving surface of the detector is changed by a change in the geometry of the radiation source or due to changes in the position of the mirrors due to changes in temperature. Drift and temperature effects are thus superimposed to the measured absorption signal.

SUMMARY OF THE INVENTION

The basic object of the present invention is to improve a measuring instrument of the above-described type such that changes in the measuring radiation due to drift and temperature have only a limited effect on the measuring result.

According to the invention, an optical absorption measuring instrument is provided for determining the percentage of a component in a fluid. A radiation source emitting measuring beams and at least one detector with a receiving surface sensitive to the measuring beams is at a first limiting surface of a measuring chamber containing the fluid. At least two plane mirrors are at a second limiting surface of the measuring chamber. The second limiting surface is located opposite the first limiting surface. The plane mirrors are positioned at the second limiting surface such that the measuring beams emitted by the radiation source are deflected to the detector. The surface of each plane mirror is dimensioned to be such that its illuminated surface in the area of the detector is larger than the receiving surface.

The advantage of the present invention is essentially that by using at least two plane mirrors for deflecting the beam, the radiation source is not imaged on the receiving surface, but the receiving surface of the detector is illuminated two-dimensionally, and the surface of each plane mirror is dimensioned to be such that the illuminated surface in the area of the detector is larger than the receiving surface of the detector. Due to the overlap of the illuminated surface and the receiving surface, it is achieved that the full receiving surface is illuminated even in case of drift and temperature effects and no variations can be observed as a result in the intensity of the measuring radiation in the area of the detector in case of temperature-related changes in the position of the plane mirrors. The overlap between the illuminated surface and the receiving surface is dimensioned to be such that the measuring beam still reaches the full receiving surface even in case of the most unfavorable constellation of the parameters. The tolerance range for the overlap can be determined most simply experimentally by exposing the measuring chamber to different temperatures and checking at each temperature whether the receiving surface of the detector is fully illuminated.

The present invention is not limited to the pure gas analysis, but it is also suitable generally for the determination of the percentage of a component, gas or liquid, in a gas or liquid sample.

It is especially advantageous to arrange a reference detector at the first limiting surface of the measuring chamber in addition to the detector. The reference detector has a reference receiving surface, which is illuminated by one of the plane mirrors, while the other plane mirror deflects the measuring beam to the detector. The surface of the plane mirror directed toward the reference detector is dimensioned to be such that the illuminated surface in the area of the reference detector is larger than the reference receiving surface.

The overlap between the illuminated surface and the receiving surface in the area of the detector or the reference detector is advantageously greater than 10% relative to the respective receiving surface. Experiments revealed that an overlap of about 10% to 20% is sufficient to suppress drift and temperature effects.

It is especially useful to design the limiting contour of the plane mirrors such that it is adapted to the receiving surface of the detector or of the reference detector. Thus, a rectangular mirror shape is suitable for a rectangular receiving surface, a round plane mirror in case of a round receiving surface, and a hexagonal mirror shape, which can be advantageously arranged in a honeycomb-like manner at the second limiting surface of the measuring chamber, in the case of a hexagonal receiving surface.

It is especially advantageous to design the plane mirrors at the second limiting surface in the form of a plane mirror matrix, wherein a first group of plane mirrors is directed toward the detector and a second group of plane mirrors toward the reference detector.

Due to the use of a plurality of plane mirrors in the form of a plane mirror matrix, contamination effects can be compensated in an especially simple manner and, moreover, no beam splitter is necessary, which would split the measuring beam between the detector and the reference detector behind the measuring chamber, because the individual plane mirrors can be positioned in the case of the plane mirror matrix such that the measuring beams are reflected directly to the detector and the reference detector.

The infrared optical measuring instrument can be manufactured in an especially simple manner and inexpensively by means of a plane mirror matrix, because the plane mirror matrix can be manufactured in connection with the second limiting surface as a one-piece molding, e.g., in the form of a plastic injection-molded part.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
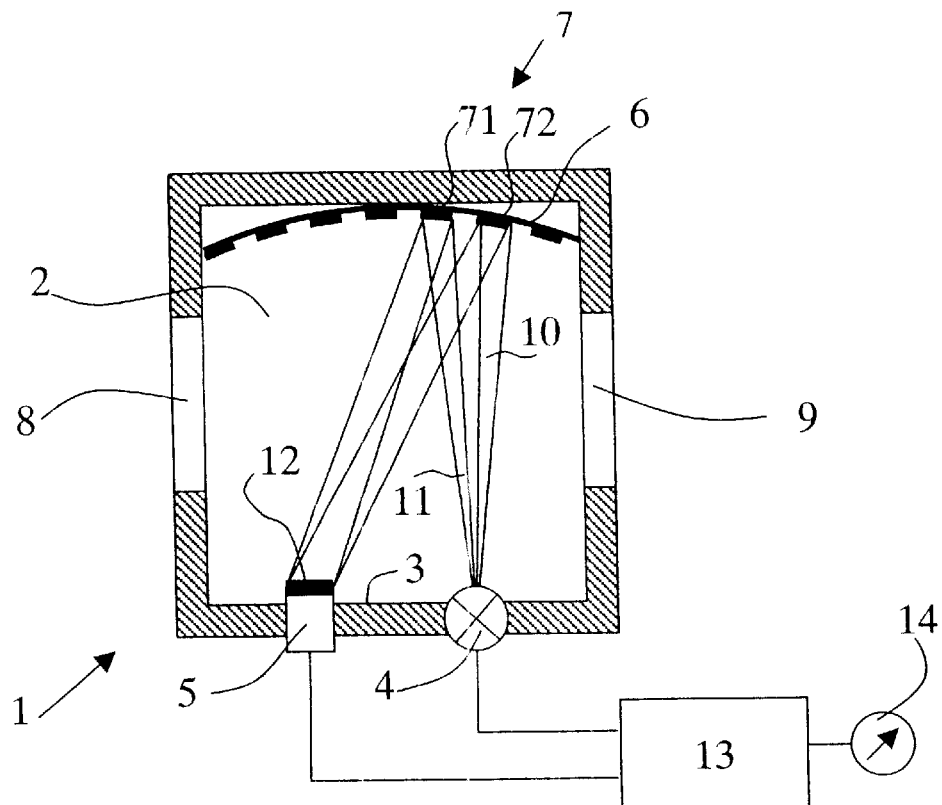
FIG. 1 is a schematic longitudinal sectional view showing the first infrared optical measuring instrument.

Referring to the drawings in particular, FIG. 1 schematically shows a first infrared optical measuring instrument 1, in which an infrared radiation source 4 and a detector 5 are arranged in a measuring chamber 2 at a first limiting surface 3 and different plane mirrors 7 in the form of a first plane mirror 71 and a second plane mirror 72 are arranged next to one another at a second limiting surface 6. The gas sample to be tested flows through the measuring chamber 2 from a measuring chamber inlet 8 to a measuring chamber outlet 9. The plane mirrors 71, 72 at the second limiting surface 6 are positioned such that the measuring beams 10, 11 emitted by the radiation source 4 are reflected onto a receiving surface 12 of the detector 5. The receiving surface 12 is the area of the detector 5 that is sensitive to the infrared radiation. The detector 5 and the radiation source 4 are connected to a control and evaluating unit 13, in which the attenuation of the measuring beams 10, 11 by the component to be detected in the gas sample is evaluated and is displayed as a concentration percentage by a display device 14.

Figure 2:
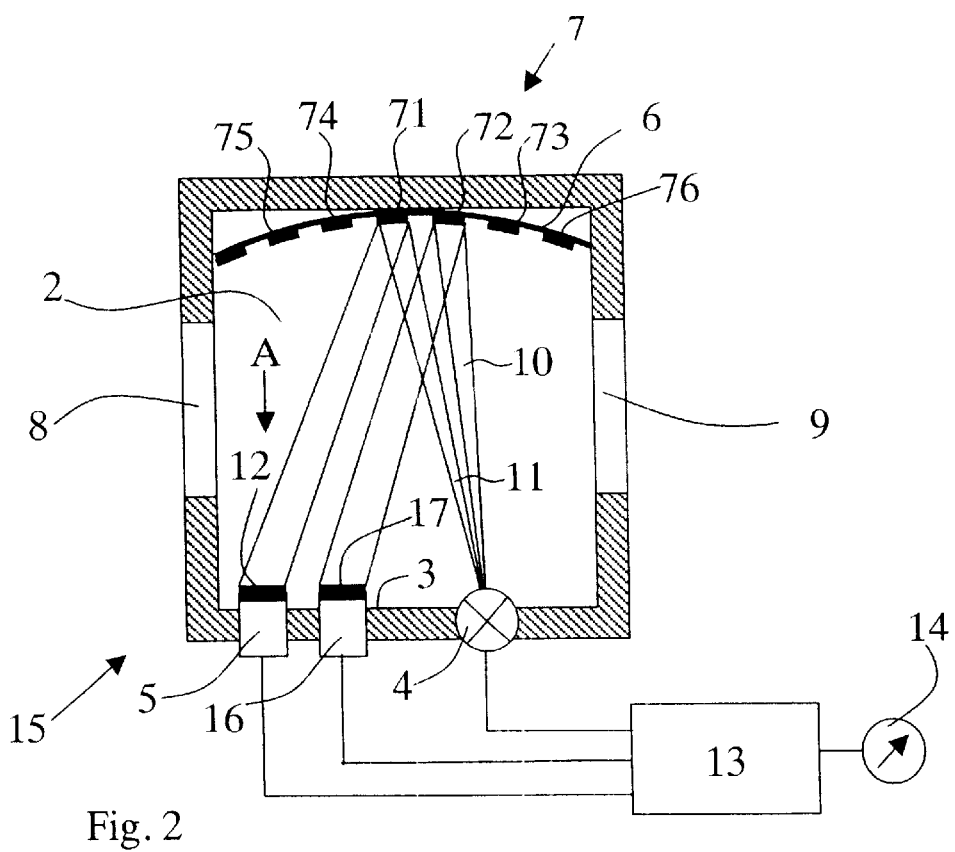
FIG. 2 is a schematic longitudinal sectional view of a second infrared optical measuring instrument.

FIG. 2 schematically illustrates a second infrared optical measuring instrument 15, in which a reference detector 16 with a reference receiving surface 17 is additionally present at the first limiting surface 3 compared with the first infrared optical measuring instrument 1 according to FIG. 1 Identical components are designated by the same reference numbers as in FIG. 1. The plane mirrors 71, 72 at the second limiting surface 6 are directed such that the first measuring beam 11 is deflected by the first plane mirror to the detector 5 and the second measuring beam 10 is deflected by the second plane mirror 72 to the reference detector 16. The other plane mirrors 73, 74, 75, 76 located at the second limiting surface 6 are positioned such that the measuring beams are alternatingly deflected to the detector 5 and to the reference detector 16. The plane mirrors 71, 73, 75 reflect measuring beams to the detector 5 and the plane mirrors 72, 74, 76 are directed toward the reference detector 16. The path of rays with the measuring beams 10, 11 is shown for the plane mirrors 71, 72 only for the sake of greater clarity. Due to the use of a plurality of plane mirrors 7 at the second limiting surface and the mutual orientation of the plane mirrors 7 toward the detector 5 and the reference detector 16, contamination effects within the measuring chamber 2 can be compensated in an especially simple manner, because they affect individual plane mirrors only.

Figure 3:
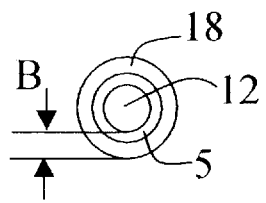
FIG. 3 is a view of an illuminated surface of a round plane mirror in the area of the detector in viewing direction "A" according to FIG. 2.

FIG. 3 shows a top view of the detector 5 with its receiving surface 12 in the viewing direction A according to FIG. 2. An illuminated surface 18, which is larger than the receiving surface 12, is illuminated by the plane mirror 71, FIG. 2, in the area of the detector 5, and there is an overlap B between the receiving surface 12 and the illuminated surface 18. The plane mirror 71 has a circular limiting contour. The overlap B, which is shown in FIG. 3 as an enlarged view, is on the order of magnitude of 10% to 20% of the receiving surface 12.

Figure 4:
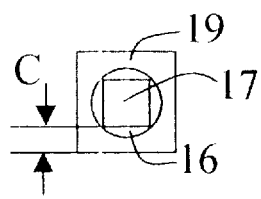
FIG. 4 is a view of an illuminated surface of a square plane mirror in the area of the reference detector in viewing direction "A" according to FIG. 2.

Compared with this, FIG. 4 shows, in the same view as does FIG. 3, a top view of the reference detector 16 with a square reference receiving surface 17. The plane mirror 72 is likewise square and leads to a square illuminated surface 19 with the overlap C. The overlap C is on the order of magnitude of 10% to 20% of the reference receiving surface 17.

Figure 5:
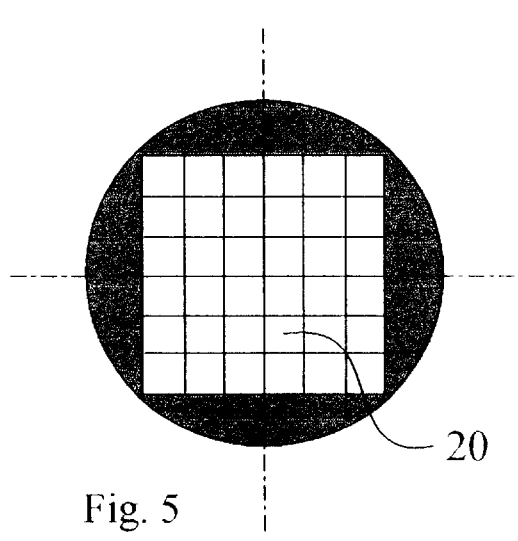
FIG. 5 is a schematic view showing a first plane mirror matrix.
Figure 6:
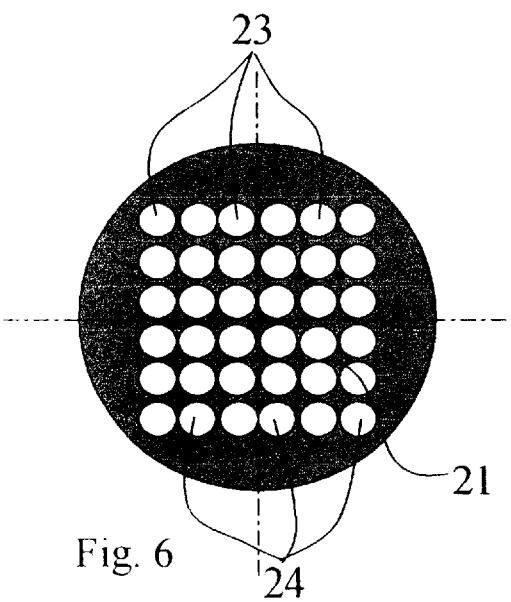
FIG. 6 is a schematic view showing a second plane mirror matrix.
Figure 7:
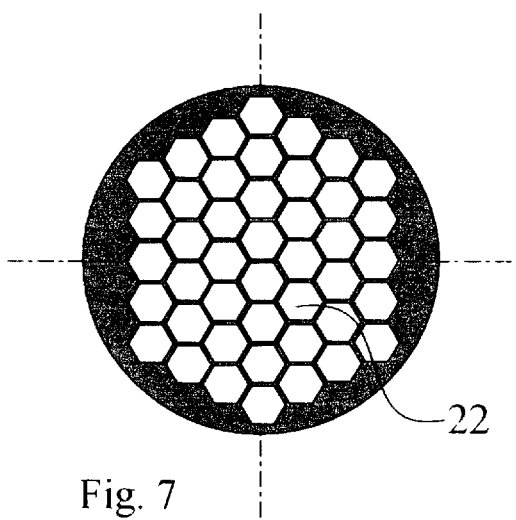
FIG. 7 is a schematic view showing a third plane mirror matrix.

FIGS. 5, 6 and 7 show different embodiments of a plane mirror matrix 20, 21, 22, in which the plane mirror matrix 20 contains plane mirrors with square limiting contour, the plane mirror matrix 21 contains plane mirrors with round limiting contour, and the plane mirror matrix 22 contains plane mirrors with hexagonal limiting contour. Depending on the contour of the cross section of the receiving surface 12 of the detector 5 and of the reference receiving surface 17 of the reference detector 16, a plane mirror matrix 20, 21, 22 adapted to the receiving surfaces 12, 17 is selected and fastened at the second limiting surface 6, FIGS. 1, 2. If only one detector, as in FIG. 1, is present, all plane mirrors of the plane mirror matrix 21 are directed toward the detector 5. If a reference detector 16, as in FIG. 2, is also present additionally, a first plane mirror group 23 is directed toward the detector 5 and a second plane mirror group 24 toward the reference detector 16. The detectors 5, 16 thus obtain the measuring beams from the radiation source 4 by direct reflection, without beam splitting by means of a beam splitter, not shown in the figures, having to be performed.

While specific embodiments of the invention have been shown and described in detail to illustrate the application of the principles of the invention, it will be understood that the invention may be embodied otherwise without departing from such principles.

What is claimed is:

1. An optical absorption measuring instrument for determining the percentage of a component in a fluid, the measuring instrument comprising:

a measuring chamber containing the fluid;

a radiation source emitting measuring beams;

at least one detector with a receiving surface sensitive to the measuring beams at a first limiting surface of said measuring chamber;

at least two plane mirrors at a second limiting surface of said measuring chamber, said second limiting surface being located opposite said first limiting surface, said plane mirrors being positioned at said second limiting surface such that the measuring beams emitted by said radiation source are deflected to the detector, wherein the surface of each plane mirror is dimensioned to be such that an illuminated surface in the area of said at least one detector is larger than said receiving surface.

2. A measuring instrument in accordance with claim 1, wherein a reference detector with a reference receiving surface is provided at said first limiting surface and one of said plane mirrors is directed toward said at least one detector and the other of said plane mirrors is directed toward the reference detector, wherein the surface of the plane mirror directed toward the reference detector is dimensioned to be such that an illuminated surface in the area of the reference detector is larger than the reference receiving surface.

3. A measuring instrument in accordance with claim 2, wherein the limiting contour of said plane mirrors is respectively adapted to the limiting contour of the respective receiving surfaces.

4. A measuring instrument in accordance with claim 1, wherein the overlap between the illuminated surface and the receiving surface is greater than 10% relative to the receiving surface.

5. A measuring instrument in accordance with claim 1, wherein the limiting contour of said plane mirrors is adapted to the limiting contour of said receiving surface.

6. A measuring instrument in accordance with claim 1, wherein the plane mirrors are arranged as a plane mirror matrix in said measuring chamber.

7. A measuring instrument in accordance with claim 6, wherein a first plane mirror group of said plane mirror matrix is directed toward the detector and a second plane mirror group of said plane mirror matrix is directed toward the reference detector.

8. An optical absorption measuring instrument for determining the percentage of a component in a fluid, the measuring instrument comprising:
  a measuring chamber for a fluid to be measured, said chamber having a first limiting surface and a second limiting surface;
  a radiation source emitting measuring radiation into the chamber;
  a detector with a receiving surface sensitive to the measuring radiation, said receiving surface being provided at or adjacent to said first limiting surface;
  a plurality of plane mirrors at or adjacent to said second limiting surface, said plane mirrors being located opposite said first limiting surface, said plane mirrors being positioned such that measuring radiation emitted by said radiation source is deflected toward said detector, wherein a surface of at least one of said plane mirrors is dimensioned to be such that an illuminated surface in an area of said detector is larger than said receiving surface.

9. A measuring instrument in accordance with claim 8, further comprising:
  a reference detector with a reference receiving surface at or adjacent to said first limiting surface, one of said plane mirrors being directed toward said detector and another of said plane mirrors being directed toward the reference detector, wherein the surface of the plane mirror directed toward the reference detector is dimensioned to be such that an illuminated surface in the area of the reference detector is larger than the reference receiving surface.

10. A measuring instrument in accordance with claim 9, wherein the limiting contour of said plane mirrors is respectively adapted to the limiting contour of the respective receiving surfaces.

11. A measuring instrument in accordance with claim 8, wherein overlap between the illuminated surface and the receiving surface is greater than 10% relative to the receiving surface.

12. A measuring instrument in accordance with claim 8, wherein the limiting contour of said plane mirrors is adapted to the limiting contour of said receiving surface.

13. A measuring instrument in accordance with claim 8, wherein the plane mirrors are arranged as a plane mirror matrix in said measuring chamber.

14. A measuring instrument in accordance with claim 13, wherein a first plane mirror group of said plane mirror matrix is directed toward the detector and a second plane mirror group of said plane mirror matrix is directed toward the reference detector.

15. A method for determining the percentage of a component in a fluid by optical absorption measuring, the method comprising the steps of:
  providing a measuring chamber for a fluid to be measured having a first limiting surface and a second limiting surface;
  emitting measuring radiation into the chamber with a radiation source;
  providing a detector with a receiving surface sensitive to the measuring radiation at or adjacent to the first limiting surface;
  providing a plurality of plane mirrors at or adjacent to the second limiting surface;
  locating the plane mirrors opposite the first limiting surface, the plane mirrors being positioned such that measuring radiation emitted by the radiation source is deflected toward the detector; and
  dimensioning at least one of the plane mirrors such that an illuminated surface in an area of the detector is larger than the receiving surface.

16. A method in accordance with claim 15, further comprising:
  providing a reference detector with a reference receiving surface at or adjacent to the first limiting surface;
  directing one of the plane mirrors toward the detector;
  directing another of the plane mirror toward the reference detector;
  dimensioning the surface of the plane mirror directed toward the reference detector such that an illuminated surface in the area of the reference detector is larger than the reference receiving surface.

17. A method in accordance with claim 15, wherein the overlap between the illuminated surface and the receiving surface is greater than 10% relative to the receiving surface.

18. A method in accordance with claim 15, wherein the limiting contour of the plane mirrors is adapted to the limiting contour of the receiving surface.

19. A method in accordance with claim 15, wherein the limiting contour of the plane mirrors is respectively adapted to the limiting contour of the respective receiving surfaces.

20. A method in accordance with claim 15, wherein plane mirrors are arranged as a plane mirror matrix in the measuring chamber including a first plane mirror group of the plane mirror matrix directed toward the detector and a second plane mirror group of the plane mirror matrix directed toward the reference detector.

* * * * *